United States Patent [19]

Colla et al.

[11] 4,142,400
[45] Mar. 6, 1979

[54] NITROGEN DIOXIDE SENSING ELEMENT AND METHOD OF SENSING THE PRESENCE OF NITROGEN DIOXIDE

[75] Inventors: Jeannine O. Colla, Whitefish Bay; Paul E. Thoma, Burlington, both of Wis.

[73] Assignee: Johnson Controls, Inc., Milwaukee, Wis.

[21] Appl. No.: 774,765

[22] Filed: Mar. 7, 1977

[51] Int. Cl.² .................. G01N 27/12; H01C 13/00
[52] U.S. Cl. ............................................. 73/23; 338/34
[58] Field of Search ............... 73/23, 27 R; 338/34, 338/35; 23/254 E

[56] References Cited

U.S. PATENT DOCUMENTS

| 3,045,198 | 7/1962 | Dolan et al. ............... 338/35 X |
| 3,645,999 | 2/1972 | Byrd ............................ 23/254 E X |
| 3,695,848 | 10/1972 | Taguchi ...................... 73/27 R X |
| 3,891,958 | 6/1975 | Wakabayashi ............ 338/34 X |

Primary Examiner—Charles A. Ruehl
Attorney, Agent, or Firm—Andrus, Sceales, Starke & Sawall

[57] ABSTRACT

An element for sensing the presence of nitrogen dioxide gas in the environment. The element comprises a film of a pyrolyzed polyaromatic polymer having semi-conductive properties which is mounted on an electrically non-conductive base. Electrical leads are attached at spaced locations to the film and are connected in an electrical circuit with a signalling or control mechanism. The presence of nitrogen dioxide gas will cause a change in the electrical characteristics of the film to thereby activate the mechanism. A heating element can be associated with the base to insure constant temperature and humidity conditions.

13 Claims, 6 Drawing Figures

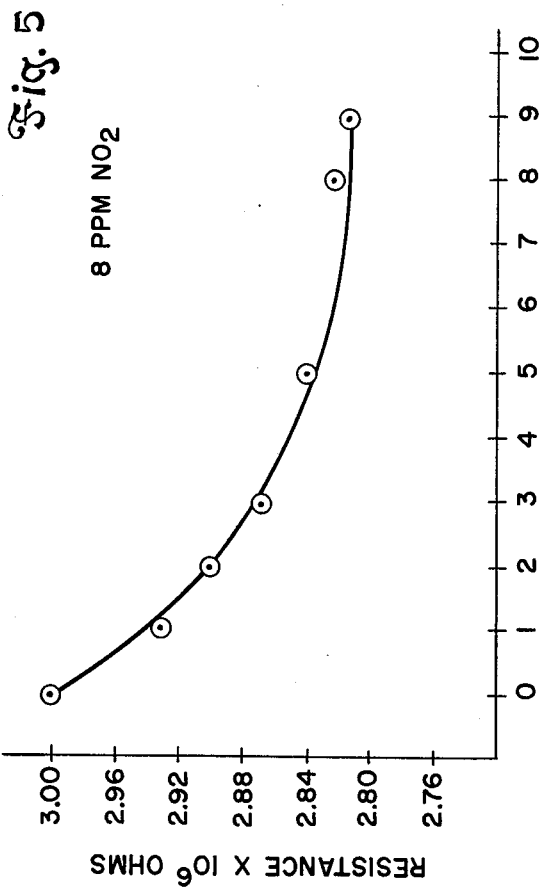
Fig. 5  8 PPM NO$_2$
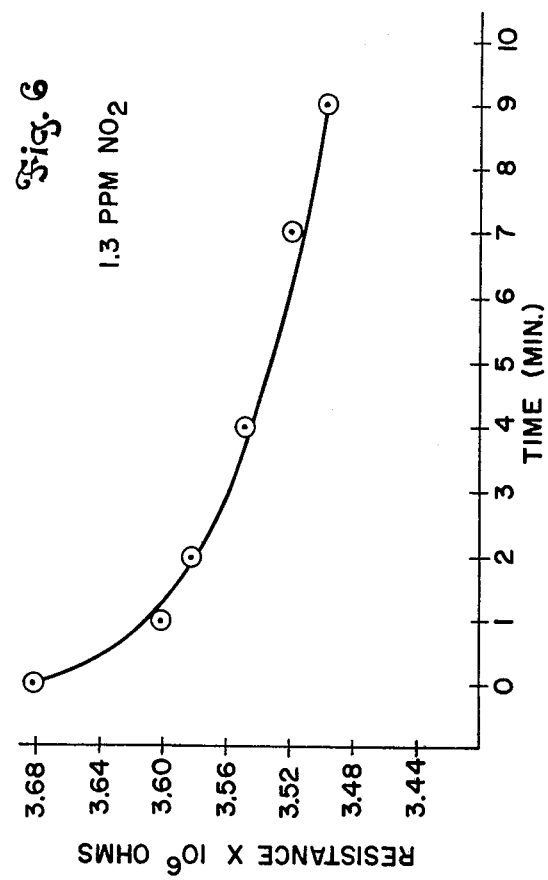
Fig. 6  1.3 PPM NO$_2$
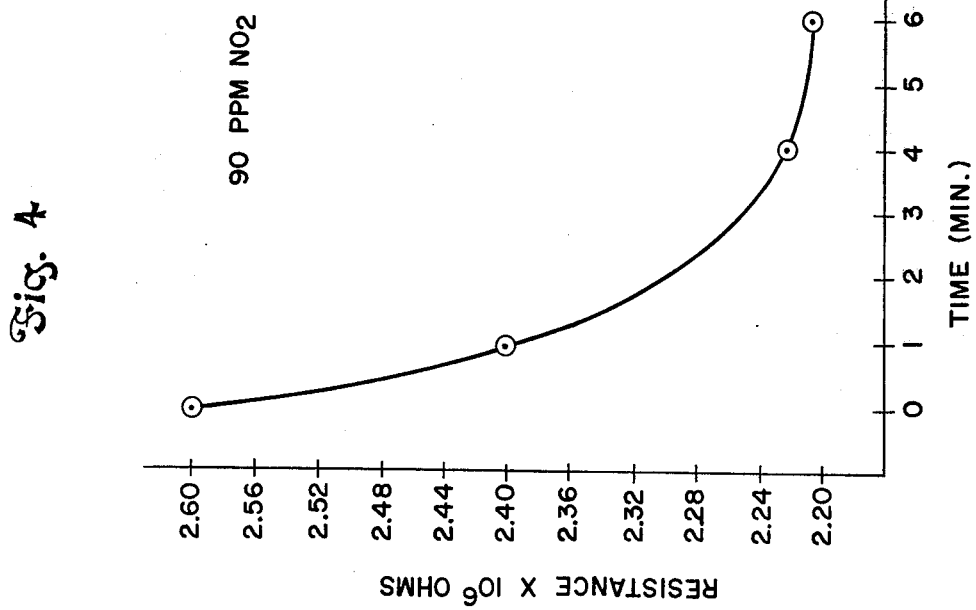
Fig. 4  90 PPM NO$_2$

NITROGEN DIOXIDE SENSING ELEMENT AND METHOD OF SENSING THE PRESENCE OF NITROGEN DIOXIDE

BACKGROUND OF THE INVENTION

Gases, such as nitrogen dioxide, carbon monoxide, sulfur dioxide, and ozone, are particularly harmful pollutant gases, particularly in urban and industrial areas. Since the development of governmental air quality standards, private industry and government agencies have spent considerable time and effort in the development of instruments for the detection and measurement of gaseous pollutants. However, at present there is no one gas sensing device on the market that is highly selective, low in cost and capable of continuous and reversible detection of gaseous pollutants.

Certain gas polutant sensors currently on the market, such as described in U.S. Pat. No. 3,603,954, sense the presence of oxidizable gases, such as hydrocarbons and carbon monoxide. Other sensors, such as that described in U.S. Pat. No. 3,045,198, sense the presence of gases having a Van der Waals constant above 9. While some of the current gas sensors are capable of continuous and reversible detection, the sensors are not specific to a particular gas. Furthermore, in most cases, the response rate of the sensors is slow, meaning that the element is slow to adsorb the gaseous pollutant and is correspondingly slow in releasing the gas.

SUMMARY OF THE INVENTION

The invention is directed to an element for sensing the presence of nitrogen dioxide gas in the environment. In accordance with the invention the element comprises a film of a polyaromatic polymer which has been pyrolyzed to provide the polymer with semi-conductive properties.

The polymeric film is mounted on an electrically nonconductive base, such as alumina, and electrical leads are attached at spaced locations to the film and connected in an electrical circuit with a signalling or control mechanism. The presence of nitrogen dioxide gas in the atmosphere will cause a change in the electrical characteristics of the film, to thereby activate the signalling or control mechanism.

To increase the reliability of the element, a heating element can be associated with the non-conductive base to insure relatively constant temperature and humidity conditions.

The element of the invention is a highly specific and low cost gas sensing transducer which responds directly and reversibly to nitrogen dioxide concentrations in the environment and is capable of continuous unattended operation with low power requirements.

Other objects and advantages will appear in the course of the following description.

DESCRIPTION OF THE DRAWINGS

The drawings illustrate the best mode presently contemplated of carrying out the invention.

In the drawings:

FIG. 4 is a curve showing the change in resistance per unit time on exposure of the element to 90 ppm of nitrogen dioxide;

FIG. 5 is a curve showing the change in resistance per unit time on exposure of the element to 8 ppm of nitrogen dioxide; and FIG. 6 is a curve showing the change in resistance per unit time on exposure of the element to 1.3 ppm of nitrogen dioxide.

DESCRIPTION OF THE PREFERRED EMBODIMENT

Figure 1:
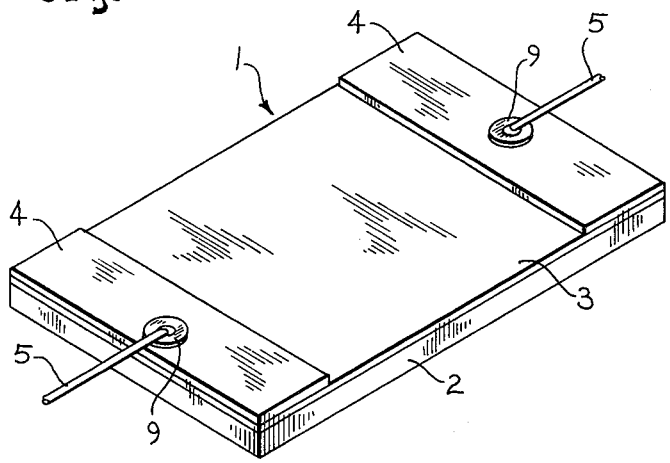
FIG. 1 is a perspective view of the sensing element of the invention.
Figure 2:
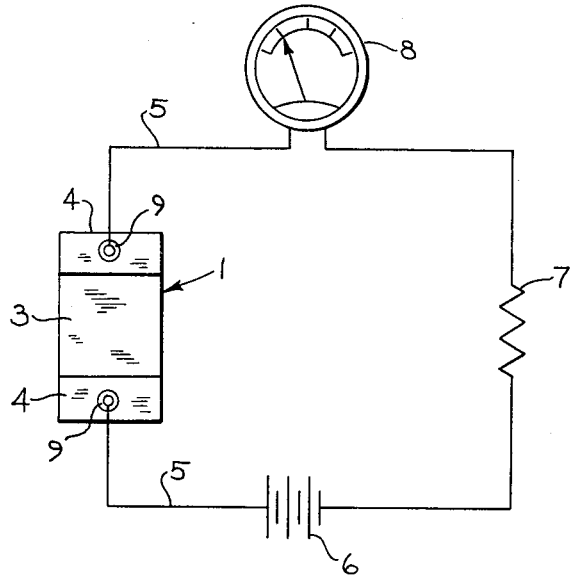
FIG. 2 is a schematic representation of a wiring diagram in which the element is connected in an electrical circuit with a signalling device.

FIG. 1 illustrates an element 1 capable of sensing the presence of nitrogen dioxide gas in the environment. The element 1 includes an electrically non-conductive base 2 and a film 3 of a pyrolyzed polyaromatic polymer is bonded to a surface of the base. Electrical terminals 4 are applied to spaced locations on the film 3, and the terminals 4 are connected by electrical leads 5 to a source of power 6, a resistor 7, and a signalling device, such as a meter 8.

The base 2 is an electrically non-conductive material, such as alumina or plastic, which is capable of withstanding the temperature and other operating conditions to which the element is exposed in service. Alumina has been shown to be a very satisfactory material for the base in that alumina has good heat conductivity, and has a coefficient of thermal expansion which is compatible with that of the pyrolyzed polymeric film 3.

The film 3 has a thickness generally in the range of 0.3 to 5 mils and is formed from a polyaromatic polymer which has been pyrolyzed to provide semi-conductive properties. The polyaromatic polymer can be a material such as a polyamide, polyamide-imide, polyimide, or a polybenzimidazole. The polybenzimidazoles, are readily prepared through the use of diphenyl esters of aromatic diacids with aromatic tetramines. For example, poly 2,2'-(m-phenylene)-5,5'-bibenzimidazole is prepared from 3,3'diaminobenzidine and diphenyl isophthalate. Certain of the polyaromatic polymers are commercially available in the form of thin films, as for example, polyimide film is sold under the trademark Kapton H by E. I. DuPont DeNemours and Co. Inc.

If the polyaromatic polymer is not available in the form of thin film, the film can be prepared by dissolving the uncured polymer in a solvent such as dimethyl formamide, dimethylacetamide, dimethyl sulfoxide, N-methylpyrrolidone, or the like, and a layer of the solvent solution is cast onto a glass plate with an adjustable strike off bar. After the solvent has evaporated, the resulting film is subjected to a curing cycle to fully crosslink the polymer. The curing is generally carried out at a temperature above 100°C., and it has been found that a three-step curing cycle is particularly satisfactory in that it prevents physical deformation of the film during the curing. As an example of the three-step curing cycle, the film is initially subjected to a temperature of 105° C. for 60 minutes, then subjected to a temperature of 150° C. for 60 minutes and this is followed by a temperature of 205° C. for 90 minutes.

Following the curing of the polymer, the film is subjected to a heat treatment which serves to pyrolyze the material and changes the electrical characteristics of the polymeric film from that of a non-conductor to a semiconductor. The pyrolysis treatment is a function of both time and temperature with the higher the temperature the shorter the duration of the treatment. In general, the polymeric film is heated in a vacuum of less than $1 \times 10^{-2}$ torr or a non-oxidizing atmosphere to a temperature in the range of 540° C. to 750°C. and maintained at this temperature for a period of time ranging from 10 minutes to 4 hours.

The pyrolysis effects a thermal degradation of the polymer with gaseous products being given off during the heat treatment. The pyrolysis is a complex chemical process, and it is believed that non-mobile unsaturated valence states exist in the semi-conductive residue after the treatment. The structure retains it aromaticity, tending toward a condensation of the aromatic ring systems. The exact mechanism of the thermal degradation is not fully established, but the resulting semiconductivity and gas sensing properties of the pyrolyzed polymer are believed to lie in the fundamental molecular structure of the starting material.

In practice, the polymeric film is placed between porous graphite plates during the pyrolysis. The graphite plates serve a dual function in that they prevent curling of the film during the heat treatment and being porous, allow the volatiles to escape during the process.

Following the pyrolysis the pyrolyzed polymeric film is bonded to the non-conductive base 2 with a suitable adhesive. Any conventional adhesive, such as epoxide resins, can be employed which are capable of withstanding the temperature and humidity conditions to which the element is exposed in service.

After the film 3 has been bonded to the non-conductive base 2, the metal terminals 4 are applied to the surface of the film. A conductive, non-oxidizing metal, such as gold, is deposited on the exposed surface of the film by vapor deposition, electroless plating, or the like. Subsequently, the film is subjected to a conventional photofabrication process by which the conductive metal is removed from the majority of the surface of the film 3, with the exception of the two areas which serve as the terminals 4, and leads 5 can then be connected to the terminals 4 with a solder or conductive epoxy resin 9.

When the element is exposed to nitrogen dioxide in the environment, the nitrogen dioxide is adsorbed and/or absorbed on the film, thereby changing the conductivity of the film due to a charge transfer taking place between the pyrolyzed polymer and the gas. It is believed that the reaction involves an electron transfer from the pyrolyzed polymer to the nitrogen dioxide. Changing conductivity of the element will create a reading in the meter 8 to signal the presence of nitrogen dioxide in the atmosphere, or alternately to actuate a control system.

While pyrolyzed polyaromatic polymers are known in the art, it is unexpected and unobvious that the pyrolyzed polyaromatic polymer would be selectively responsive to nitrogen dioxide gas, while not being sensitive to other gases, such as sulfur dioxide, halogens, hydrocarbons, or the like. This result is completely unforseen.

With an increase in temperature metallic conductors increase their resistance whereas the organic pyrolyzed polymeric film of the invention decreases its resistance, with a corresponding increase in temperature. Moreover, the resistance of the semi-conductive film decreases in the presence of moisture. Because of this the resistance of the element can vary from day to day as a function of the ambient temperature and humidity conditions. In order to stabilize the temperature and humidity conditions, a resistance type heater can be incorporated into the design of the element and its function is to maintain the element at a fixed elevated temperature where the affect of ambient humidity and temperature fluctuations will be minimized.

Figure 3:
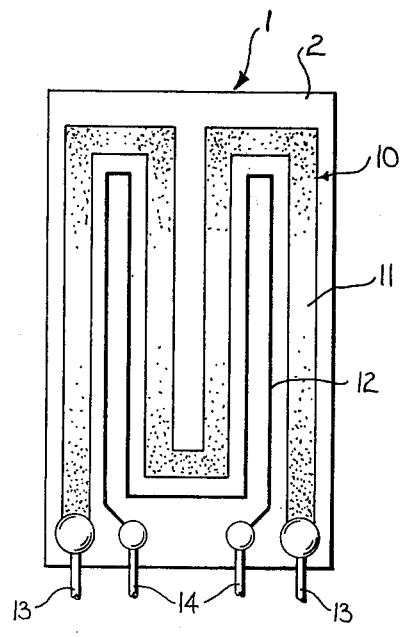
FIG. 3 is a plan view of the rear surface of a modified form of the element incorporating a resistance heating element.

In this regard, FIG. 3 shows a modified form of the invention in which a resistance type heater 10 is incorporated with the element 1. The heater includes a pair of conductive grids 11 and 12 which are printed or otherwise applied to the surface of the base 2 opposite to that which supports the film 3. The grid 11 is a resistance type heater, while the grid 12 serves as a controller. Leads 13 are connected to the grid 11 and leads 14 are connected to grid 12 and the leads are connected to a suitable source of power, not shown, in a conventional manner. With this construction the element is heated generally to a temperature above 100° C. and in the range of about 100° C. to 125° C. At this temperature, the effect of ambient variations in temperature and humidity will be minimized.

The following examples illustrate the preparation of the gas sensing element of the invention.

EXAMPLE NO. I

Polybenzimidazole was dissolved in a solvent, dimethylacetamide, and the solvent solution was cast as a film having a thickness of 2.0 mils onto a glass plate with an adjustable strike off bar. After evaporation of the solvent, the film was subjected to a curing cycle consisting of 105° C. for 60 minutes, 150° C. for 60 minutes, and 205° C. for 90 minutes to fully crosslink the polymer.

Sections of the cured film having a size of 0.5 inch by 0.5 inch were placed between porous flat graphite plates and subjected to heat treatment in a vacuum furnace. The film sections were subjected to a temperature of 593.3° C. for 60 minutes and vacuum cooled to ambient temperature, thereby resulting in the pyrolysis of the film and change in state from non-conductor to semiconductor.

The pyrolyzed film sections were bonded to an alumina substrate with an epoxy resin, and a layer of gold was plated on the exposed surface of the film by vapor deposition. The plated film was then subjected to a photofabrication process which removed the gold from the surface of the film with the exception of two areas which constituted the terminals. Electrical leads were then bonded to the terminals on the element.

The element was connected in an electrical circuit with a source of power and a Keithley electrometer Model 610C. The electrometer showed a measurable change in the resistance when the element was exposed to a little as 1.3 ppm of nitrogen dioxide in the atmosphere.

EXAMPLE NO. II

Thin polyimide film (Kapton H a product of E. I. DuPont DeNemours and Co. Inc.) having a thickness of 1.0 mil was initially plated with gold by an electroless plating method. The electroless plating was followed by photofabrication and etching to remove the gold plating from the gas sensing area of the film.

The film was then subjected to a pyrolysis treatment by heating in a vacuum at 607.2° C. for 60 minutes. Following the heat treatment the pyrolyzed film sections each having a size of approximately 0.5 inch by 0.5 inch were mounted on an alumina substrate with an epoxy resin.

The element was connected in an electrical circuit with a Keithley electrometer Model 610C and was exposed to various concentrations of nitrogen dioxide as shown in the curves of FIGS. 4, 5 and 6. FIG. 4 shows the change in resistance in ohms which occurred when the element was subjected to 90 ppm of nitrogen dioxide. As illustrated in FIG. 4, the original resistance was $2.60 \times 10^6$ ohms and after 4 minutes of exposure to this concentration of nitrogen dioxide, the resistance changed to a valve of $2.30 \times 10^6$ ohms.

The curve in FIG. 5 illustrates the results of a similar test when the element was exposed to a concentration of 8 ppm of nitrogen dooxide, while the curve of FIG. 6 illustrates the change in resistance which occurred when the element was subjected to a nitrogen dioxide concentration of 1.3 ppm. The curves of FIGS. 4–6 illustrate the substantial change in resistance that occurred in the element over a relatively short period of several minutes when exposed to various concentrations of nitrogen dioxide.

The element of the invention is a highly specific gaseous sensor which responds directly and reversibly to nitrogen dioxide concentrations in the environment.

The element of the invention can be used in various applications where it is desired to sense the presence of nitrogen dioxide gas in the environment. As an example, it can be used in plants producing nitric acid or ammonia, environmental areas of operation of high temperature combustion engines, or environments where electrical arcing may occur and nitrogen dioxide may be generated.

Various modes of carrying out the invention are contemplated as being within the scope of the following claims particularly pointing out and distinctly claiming the subject matter which is regarded as the invention.

We claim:

1. An element capable of sensing the presence of nitrogen dioxide in the environment, comprising a film of a pyrolyzed polyaromatic polymer, and electrical leads connected to said film at spaced locations, the presence of nitrogen dioxide in the environment causing a change in the electrical characteristics of the film.

2. The element of claim 1, wherein said polymer is selected from the group consisting of polyamides, polyamideimides, polyimides and polybenzimidazoles.

3. The element of claim 1, and including an electrically non-conductive base to support the film.

4. The element of claim 3, wherein said film has a thickness in the range of 0.3 to 5 mils.

5. The element of claim 3, and including heating means connected to said base for maintaining the base at a temperature substantially above ambient temperature to thereby minimize the effect of ambient temperature and humidity variations.

6. The element of claim 1, and including non-corroding metal layers disposed on a surface of said film at spaced locations, said leads being connected to said layers.

7. An element capable of sensing the presence of nitrogen dioxide in the environment, comprising a film of pyrolyzed polyaromatic polymer having nitrogen as a part of the ring structure and being electrically responsive to nitrogen dioxide, an electrically non-conductive base to support the film, and electrical leads connected to said film at spaced locations, the presence of nitrogen dioxide in the environment causing a change in the electrical characteristics of the film.

8. An element capable of sensing the presence of nitrogen dioxide gas in the environment, comprising an electrically non-conductive base, a film of pyrolyzed polyaromatic polymer secured to a surface of said base and having semi-conductor characteristics, electrical leads connected to the film at spaced locations thereon, the presence of nitrogen dioxide gas causing a change in the electrical characteristics of said film, and heating means connected to the opposite surface of the base for heating the base to a temperature substantially above ambient temperature.

9. A system for sensing the presence of nitrogen dioxide gas in the environment, comprising a sensing element including an electrically non-conductive base, and a film of a pyrolyzed polyaromatic polymer secured to a surface of said base, said element also including a pair of electrical terminals connected to the film at spaced locations thereon, a source of electrical power, signalling means, and an electrical circuit connecting said terminals, said source of power and said signaling means, the presence of nitrogen dioxide gas in the atmosphere causing a change in the electrical characteristics of said film to thereby actuate said signaling means.

10. The system of claim 9, wherein said polymer is selected from the group consisting of polyamides, polyamideimides, polyimides and polybenzimidazoles.

11. The system of claim 9, and including heating means connected to the base for heating the base to a temperature substantially above ambient temperature.

12. A method of sensing the presence of nitrogen dioxide in the environment, comprising the steps of exposing a film composed of a pyrolyzed polyaromatic polymer to a gaseous environment containing nitrogen dioxide gas, and measuring the change in electrical characteristics of said film caused by adsorption and/or absorption of said nitrogen dioxide gas.

13. The method of claim 12, wherein said polymer is selected from the group consisting of polyamides, polyamideimides, polyimides and polybenzimidazoles.

* * * * *